United States Patent

Brevard et al.

[11] Patent Number: 5,974,343
[45] Date of Patent: Oct. 26, 1999

[54] PROBE, PARTICULARY A URETHRAL PROBE, FOR HEATING OF TISSUES BY MICROWAVE AND FOR THE MEASUREMENT OF TEMPERATURE BY RADIOMETRY

[75] Inventors: Christian Brevard, Wissembourg; Michel Weiss, Gries; Bernard Loewenguth, Wissembourg; Jean-Pierre Mabire, Haguenau, all of France

[73] Assignee: Bruker SA, Wissembourg, France

[21] Appl. No.: 08/782,946

[22] Filed: Jan. 13, 1997

[30] Foreign Application Priority Data

Jan. 12, 1996 [FR] France .................... 96 00451

[51] Int. Cl.$^6$ ...................................... A61F 2/00
[52] U.S. Cl. ..................... 607/102; 607/104; 607/105
[58] Field of Search .................. 607/98, 101, 102, 607/104, 105, 113, 115, 116, 138, 143

[56] References Cited

U.S. PATENT DOCUMENTS 5,827,277  10/1998  Edwards ........................... 607/101

FOREIGN PATENT DOCUMENTS 0 317 067   5/1989   European Pat. Off. .
0 648 515   4/1995   European Pat. Off. .
WO 93/17756  9/1993  WIPO .
WO 95/01814  1/1995  WIPO .

*Primary Examiner*—Michael Peffley
*Assistant Examiner*—Rosiland Kearney
*Attorney, Agent, or Firm*—Young & Thompson

[57] ABSTRACT

A probe, particularly a urethral probe, for the heating of tissue by microwaves and for the measurement of temperature by radiometry. The probe comprises, on the one hand, at least one elongated antenna (1) formed by at least one conductive portion (2, 2') rolled up in a helicoidal manner on an elongated dielectric support (3) having a front end and a rear end, on the other hand, electrical connections (4) for the transfer of microwave signals toward and from the antenna, connected to a corresponding external generator and radiometer, and, finally, a catheter (5) covering the antenna (1) and, as the case may be, at least the portion of the electrical connections adjacent the antenna (1). The central dielectric support (3) has structure for circulation of thermostatic fluid of the antenna (1) at least present within the tubular channel delimited by the helicoidal conductor portion (2, 2'), this structure being connected to structure (6, 6', 6", 6''') for the supply and evacuation of the thermostatic fluid.

29 Claims, 11 Drawing Sheets

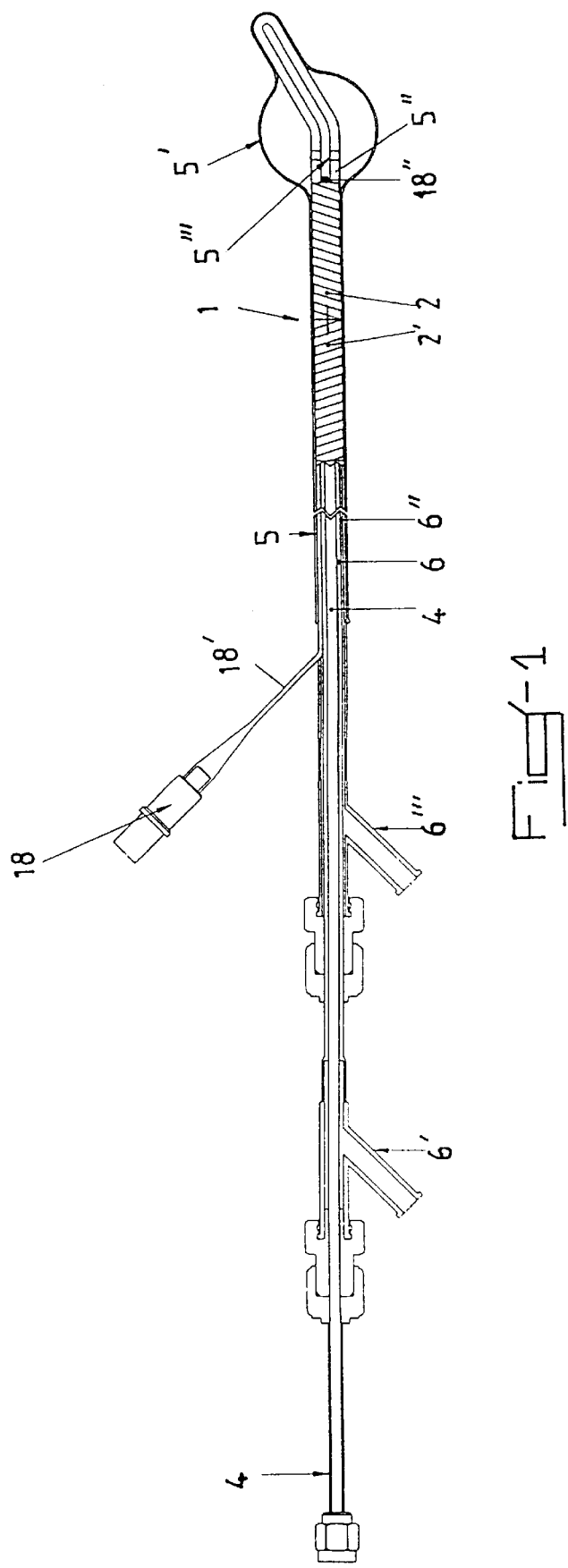

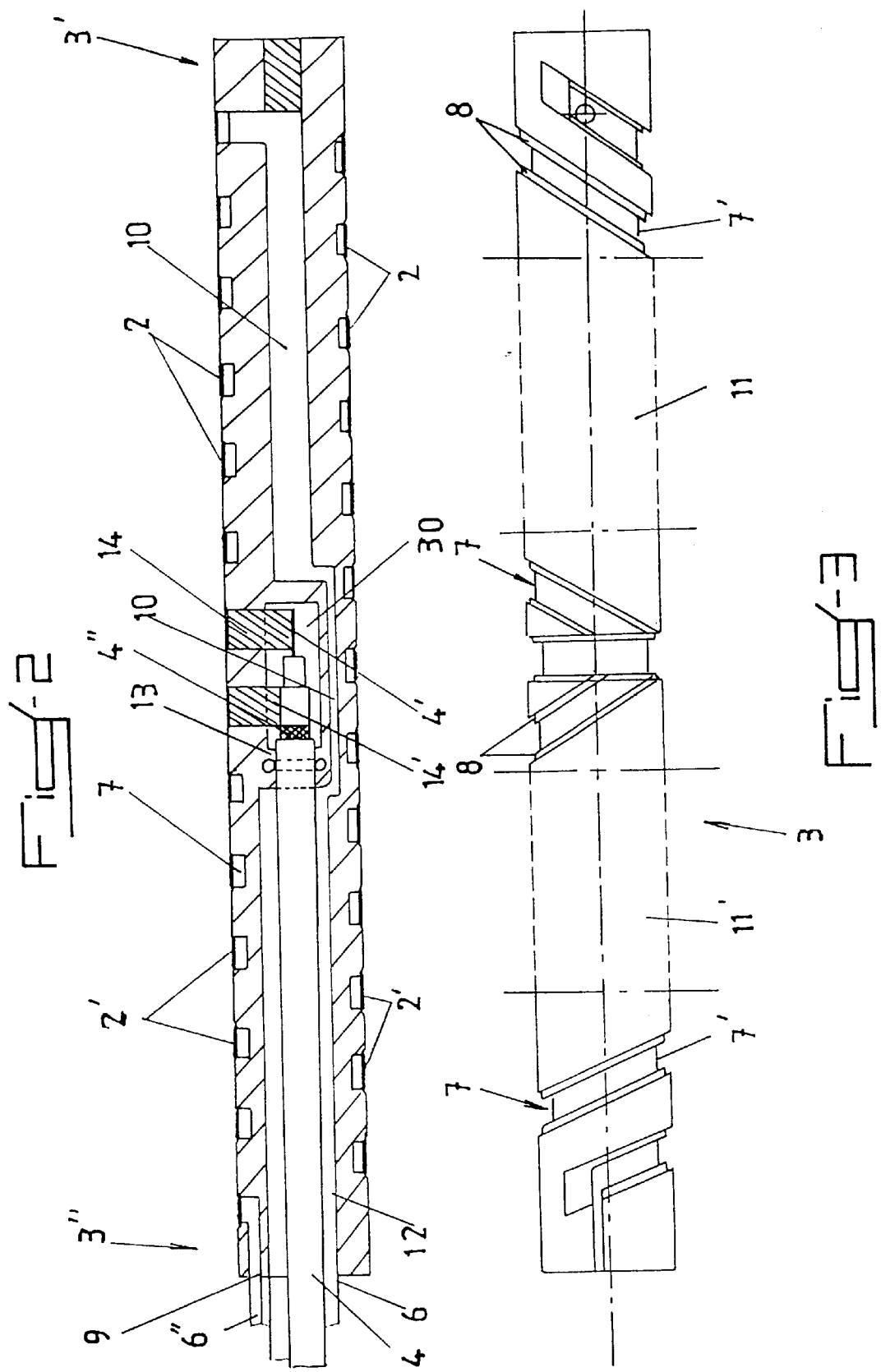

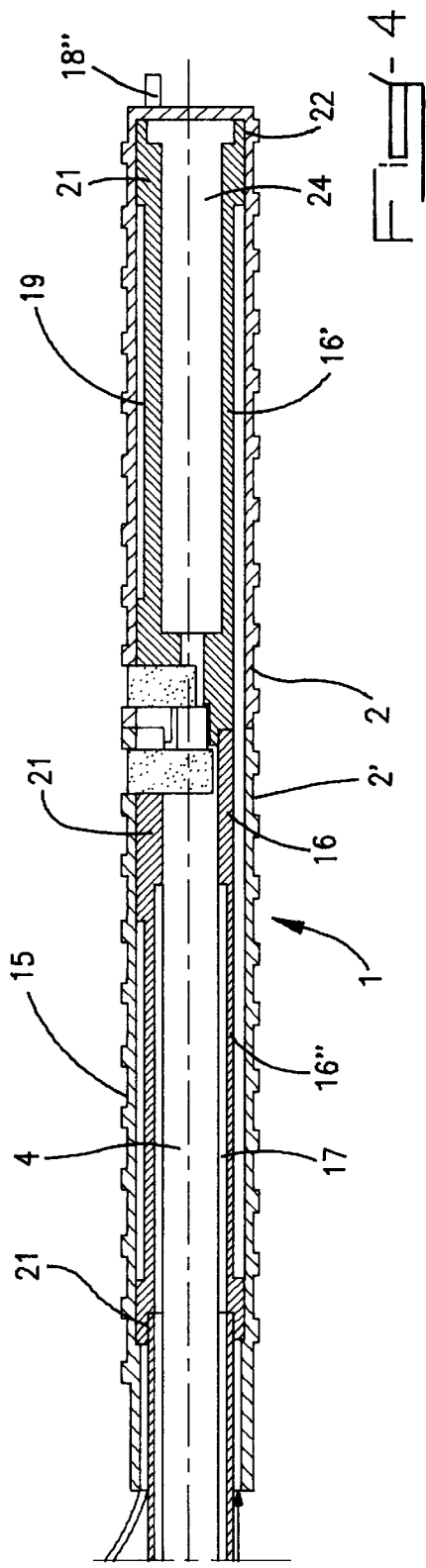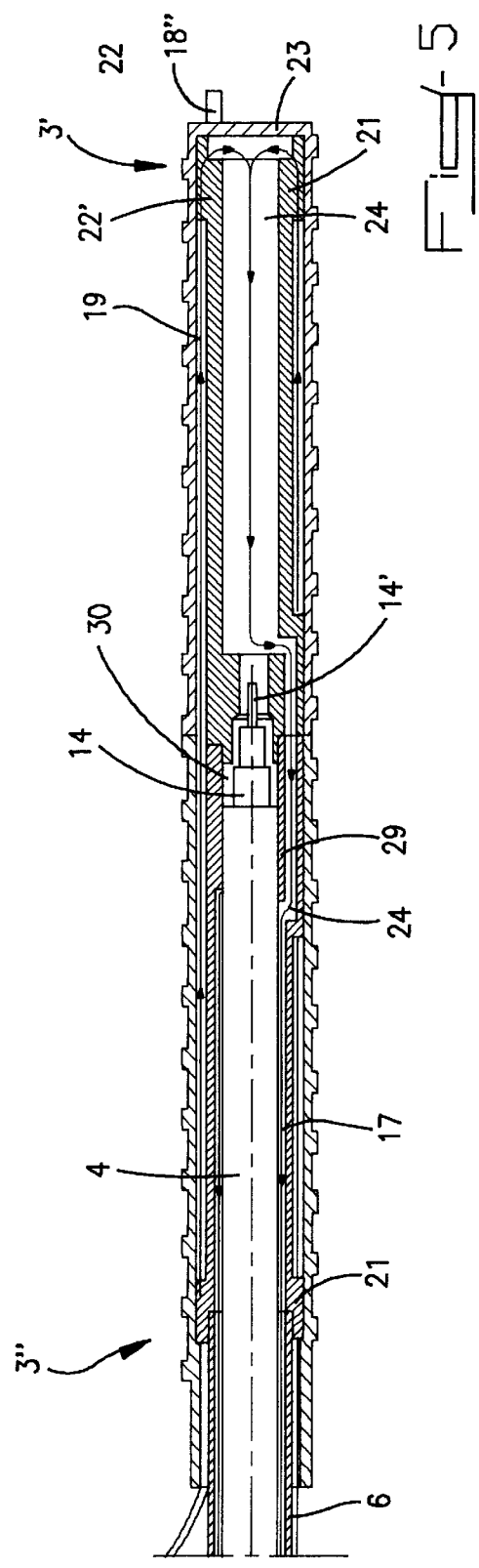

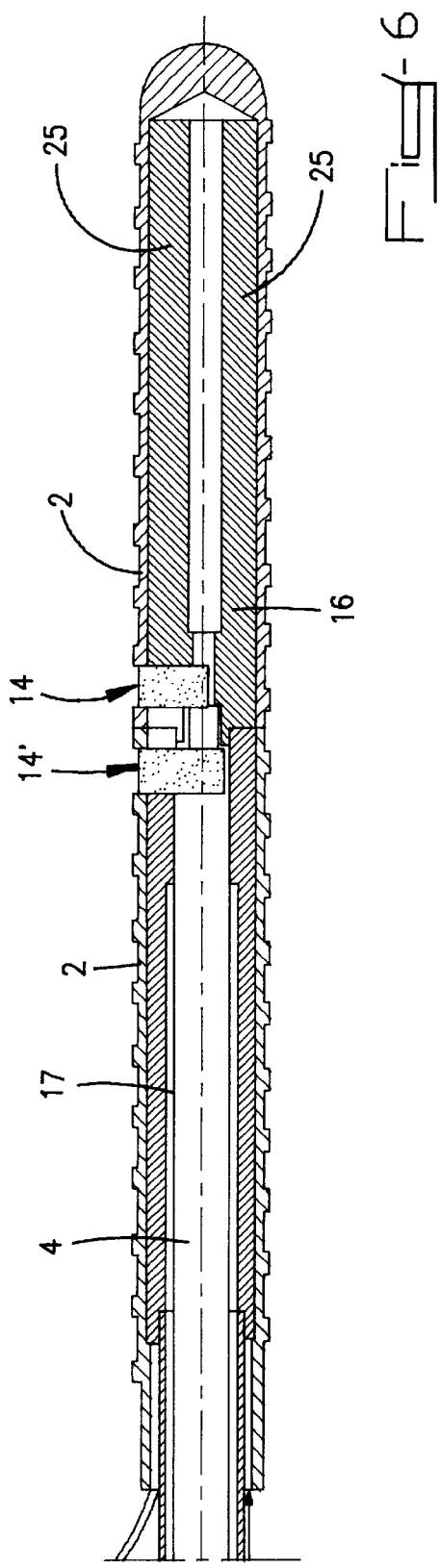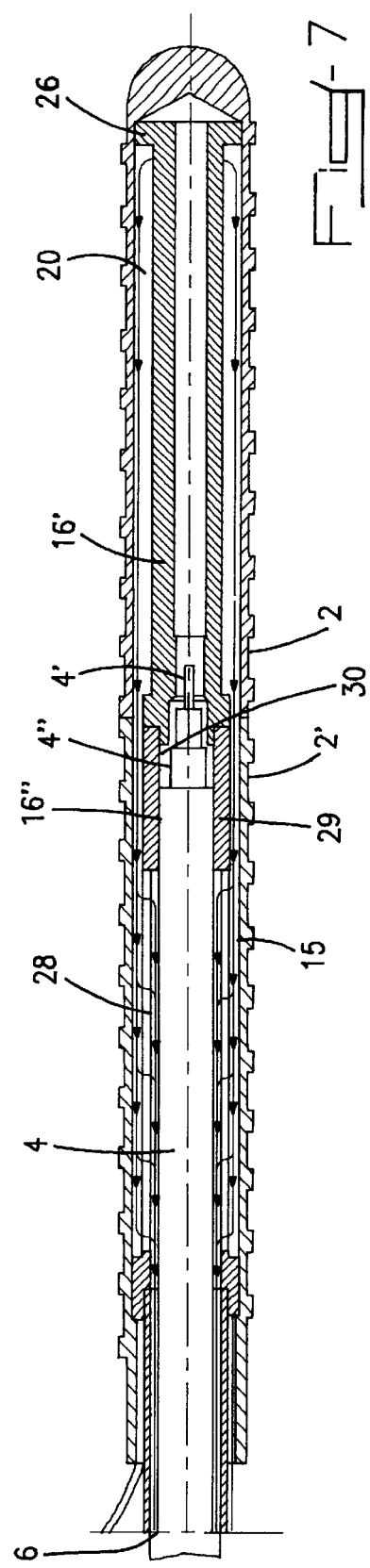

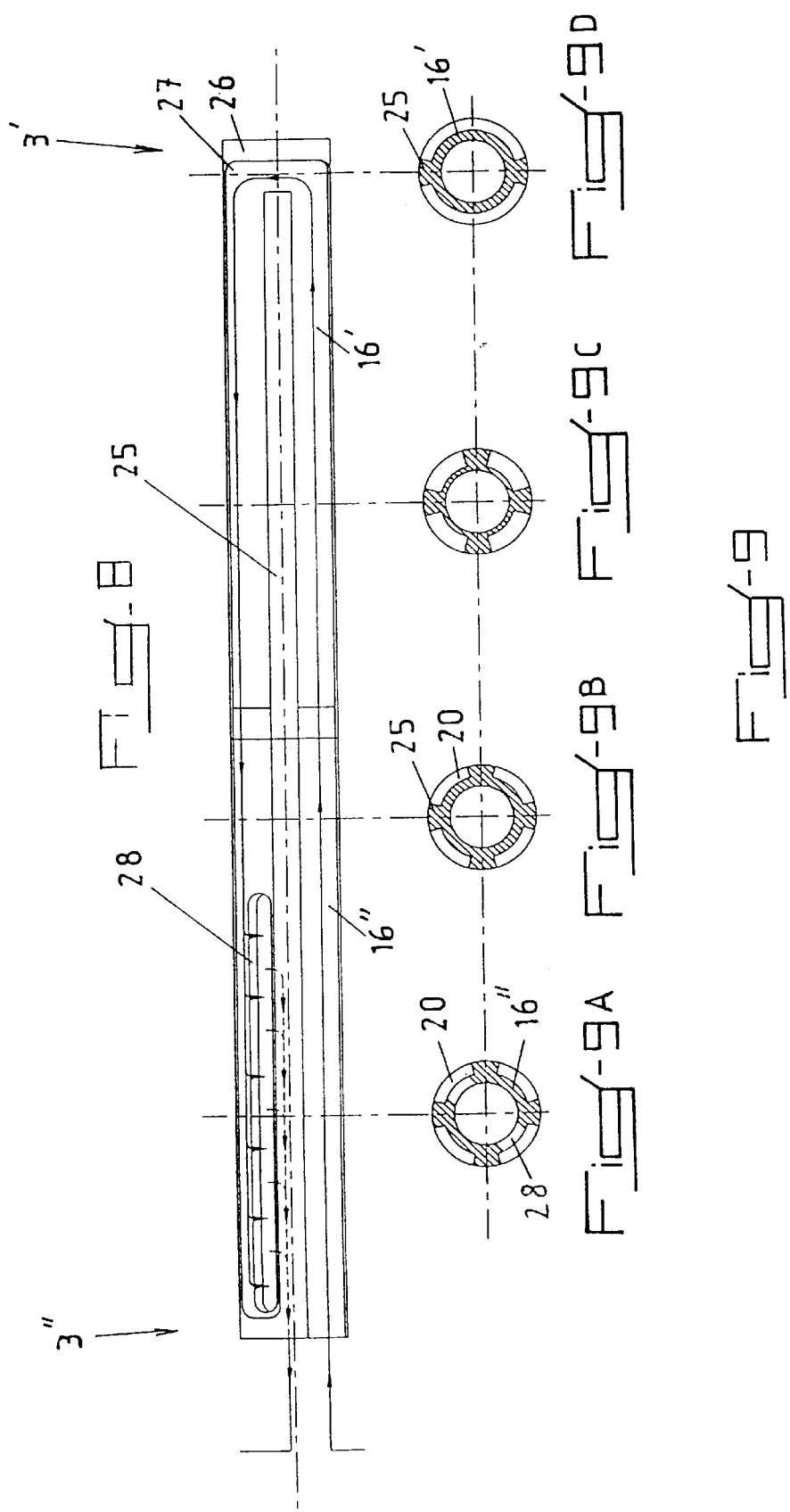

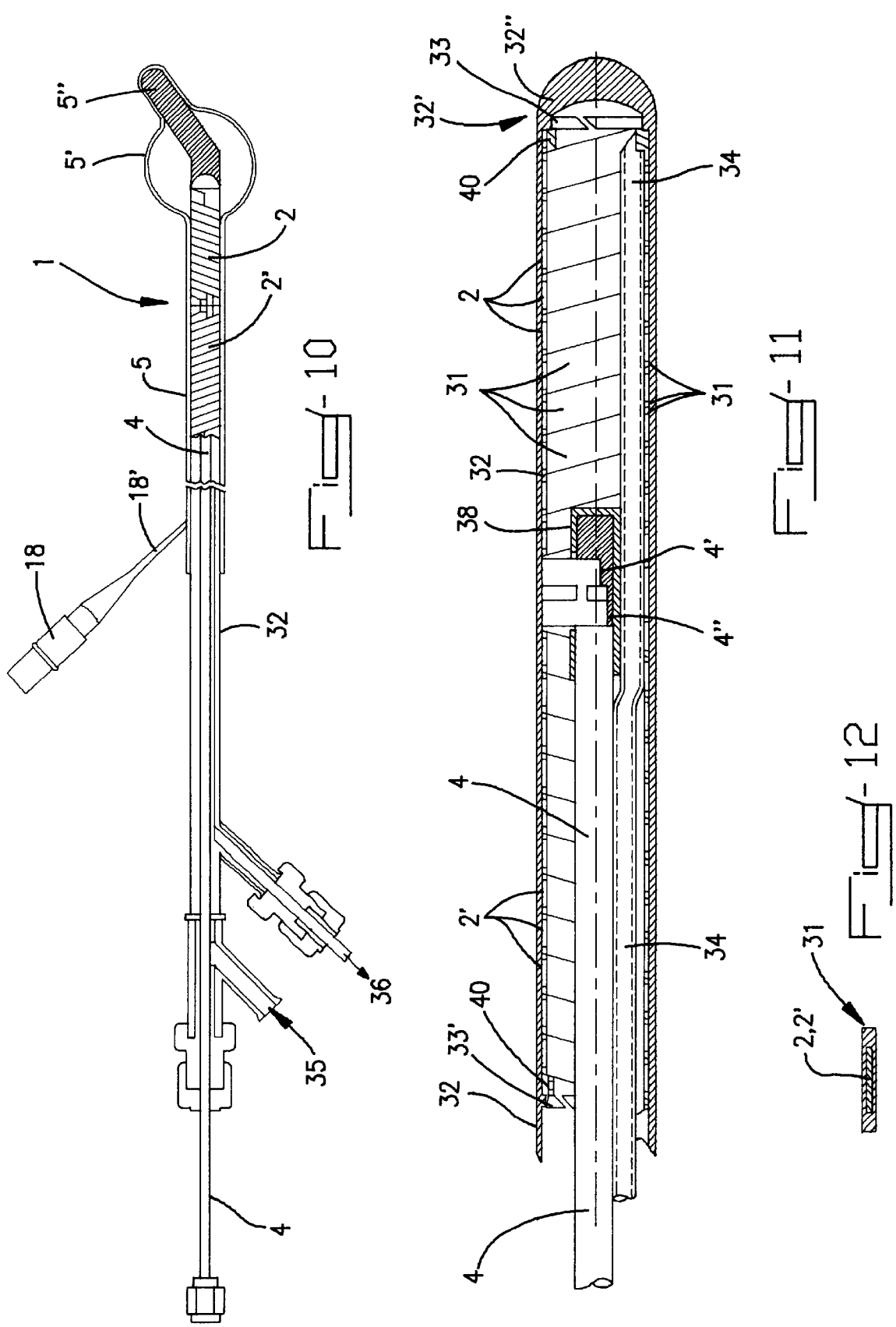

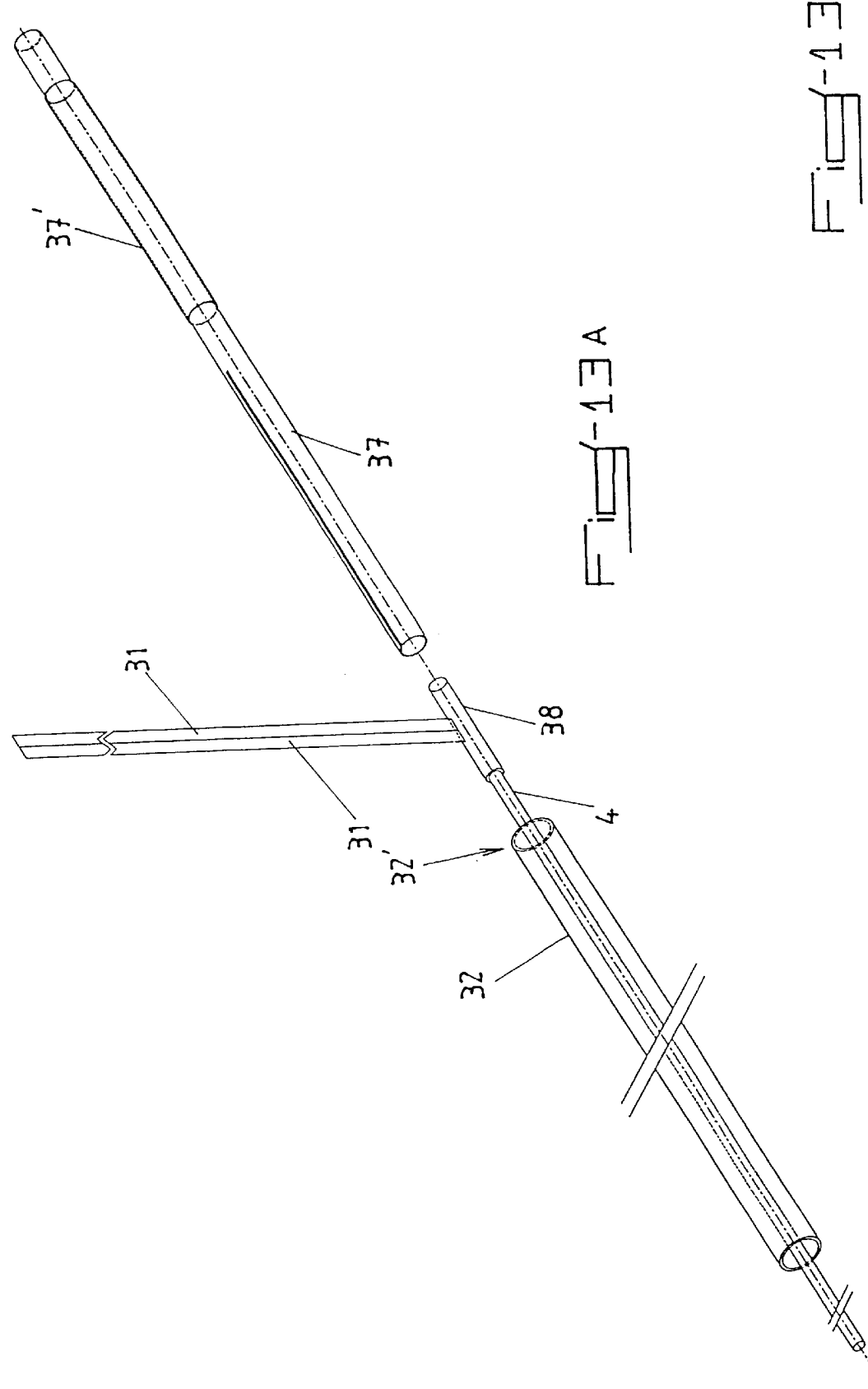

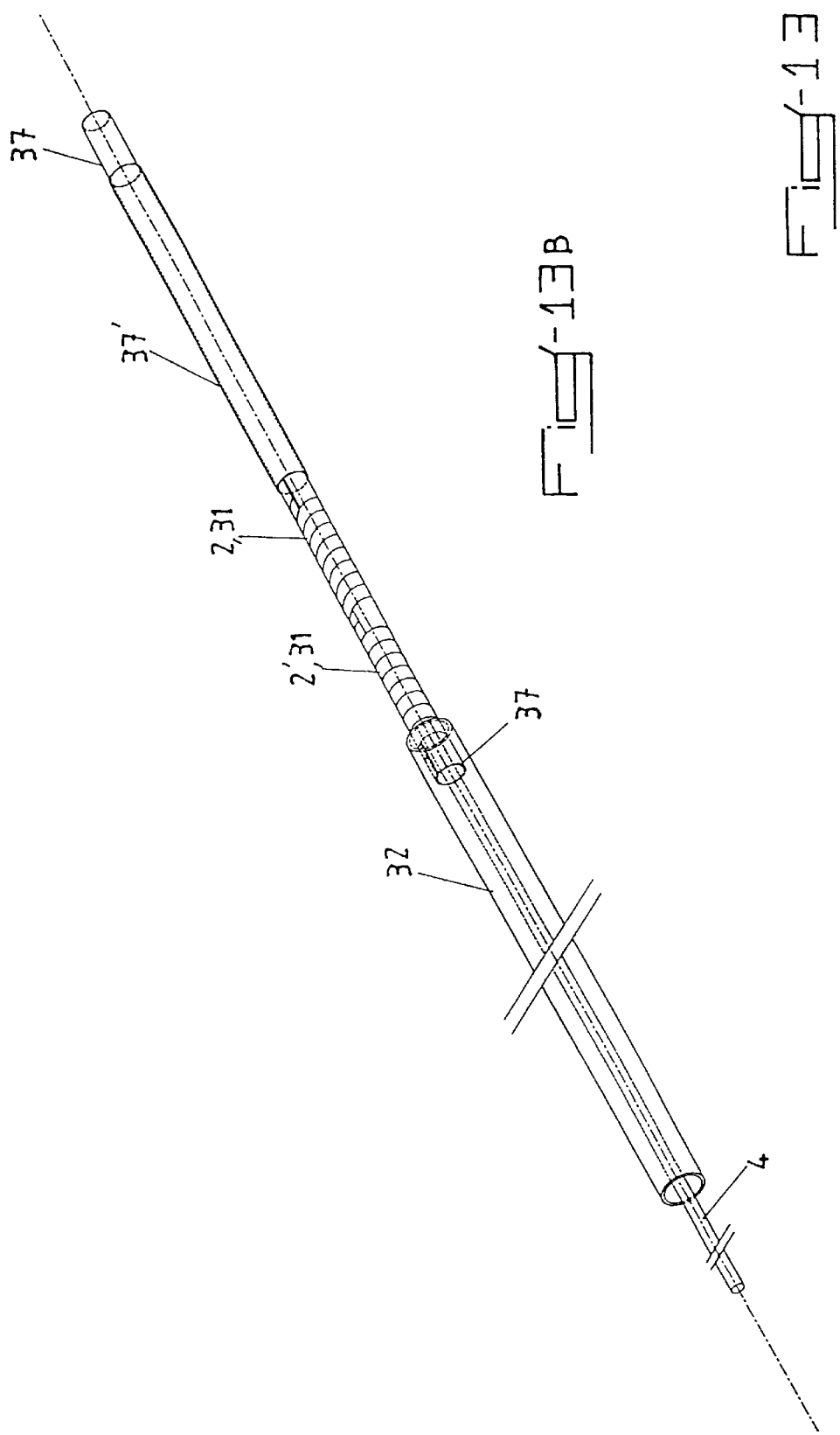

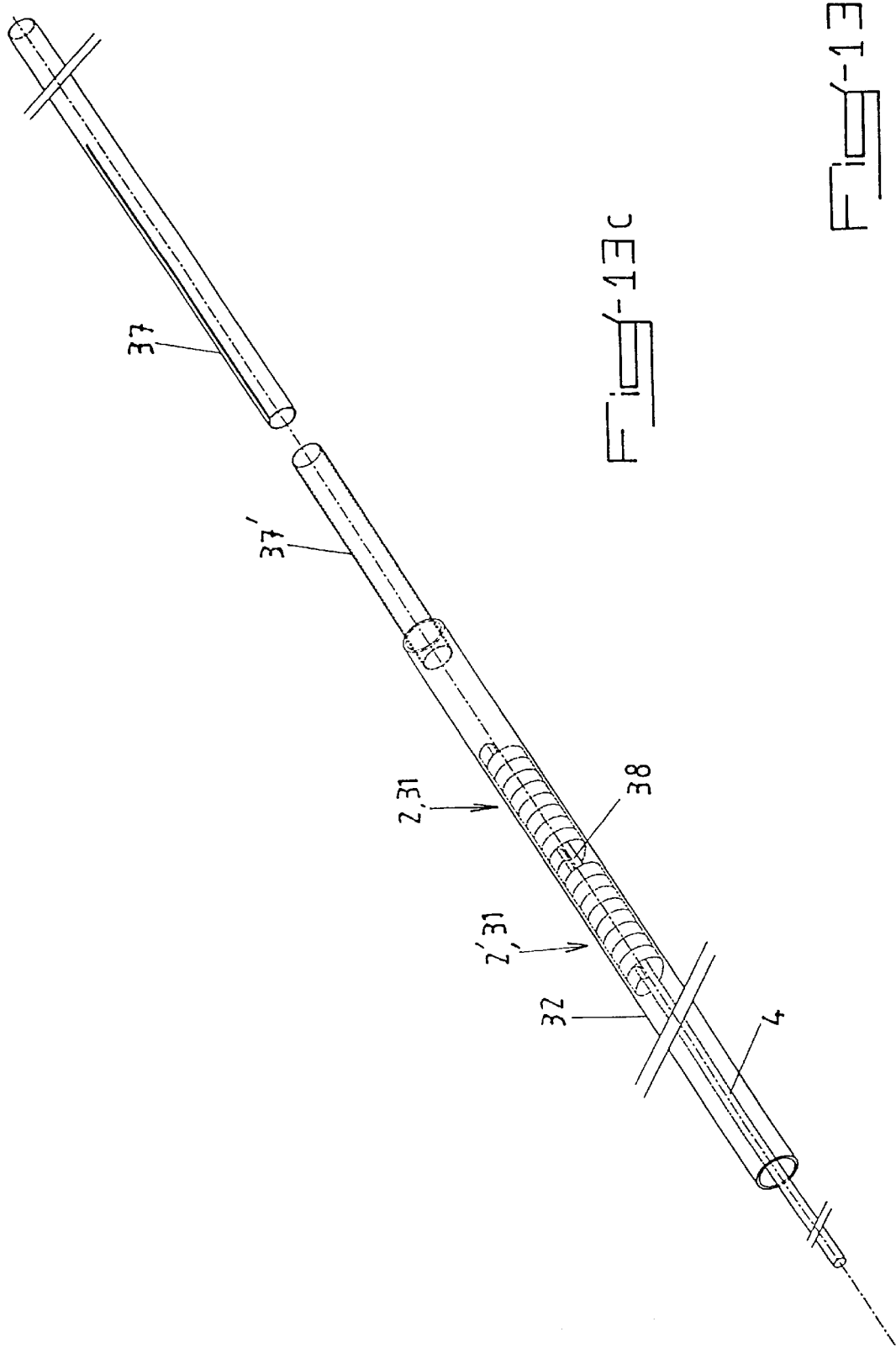

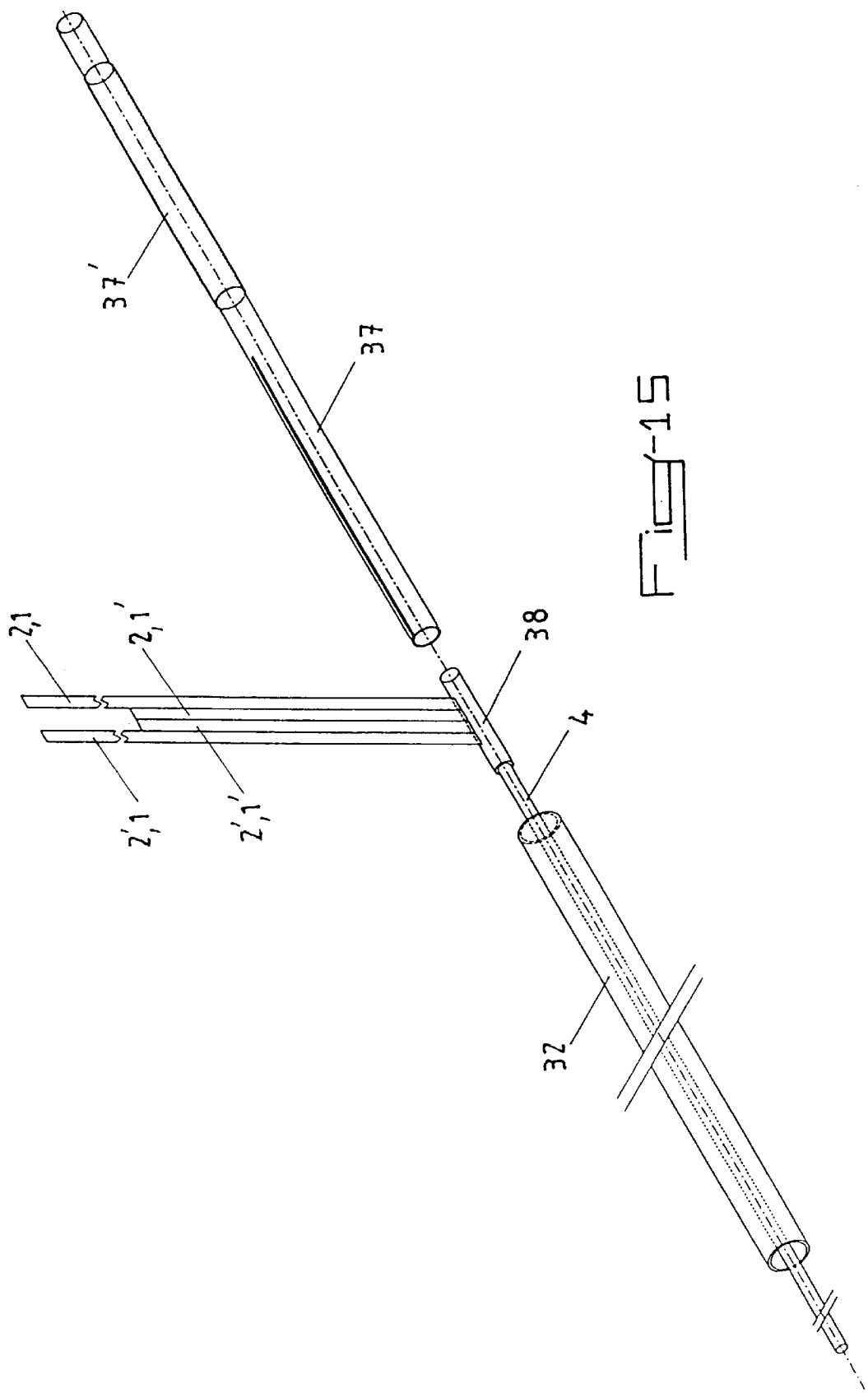

5,974,343

PROBE, PARTICULARY A URETHRAL PROBE, FOR HEATING OF TISSUES BY MICROWAVE AND FOR THE MEASUREMENT OF TEMPERATURE BY RADIOMETRY

CROSS REFERENCE TO RELATED APPLICATION

This application corresponds to French application 96 00451 of Jan. 12, 1996, the disclosure of which is incorporated herein by reference.

FIELD OF THE INVENTION

The present invention relates to the field of hyperthermal techniques and thermotherapy, more particularly probes and antennas adapted to be introduced into a conduit or a cavity of the human body, particularly of small dimension, such as a prostatic ureter, and has for its object a probe for heating tissues by microwaves and for the measurement of temperature by microwave radiometry, particularly at the level of the prostate.

BACKGROUND OF THE INVENTION

Thermometry by microwave radiometry, whose principle is well known to those skilled in the art, and of which a process for measurement is described in French patent No. 2 650 390, can preferably use a microwave detector which is constituted by the microwave emission antenna used as a receiver.

There are also already known numerous probes of the mentioned type, particularly intra urethral, having an antenna of the filament type, constituted by the bare end of a coaxial cable.

However, these known probes produce non-homogeneous heating of the surrounding tissues, by concentrating a large part of the radiated energy in a constricted volume, and do not have a heated volume coinciding with a specific volume of tissues to be heated, such as for example the prostate.

Moreover, the microwave radiation diagram of these probes having a shape different from that of their radiometric reception diagram, such probes cannot be used in an optimum manner as receiving antennas for radiometric measurement.

So as to overcome the mentioned drawbacks, it has been proposed to provide and use probes, particularly urethral, for heating by microwave emission and for the measurement of temperature by microwave radiometry, comprising on the one hand an elongated antenna formed by at least one portion of a conductor rolled up in a helicoidal manner on an elongated dielectric support having a front end and a rear end, on the other hand electrical connection means for the transfer of microwave signals toward and from said antenna, connected to a corresponding external generator and radiometer and, finally, a catheter covering said antenna and, as the case may be, at least part of the electrical connection means proximal to said antenna.

Such probes are particularly described in French patent application 2 711 066 and in European patent application 0 648 515 in the name of the applicant.

However, in the framework of new therapeutic protocols using substantially higher temperatures, it is necessary to carry out both a deep necrosis of the prostatic tissues, and a necrosis of the urethral wall, so as to create a veritable prostatic compartment. Moreover, so as to destroy the superficial nerve endings to avoid any sensation of pain, and the blood microcirculation opposing temperature rise by the thermoregulation system of the organism, high powers (70 to 90 W) are used.

There results a very high temperature rise of said radiating conductor portions and of the supply line which does not permit immediately after a given emission sequence, carrying out reliable and significant radiometric measurements by means of said conductor portions.

It has therefore been proposed to adopt the previously known solution for probes with filamentary antennas and to arrange said radiating conductor portions in a sleeve traversed by a thermostatic liquid.

Nevertheless, this thermostatic liquid surrounding the antenna constituted by said conductor portions, comprises a screen between said antenna and the surrounding tissues. Said thermostatic liquid absorbs a portion of the thermal noise emitted by the surrounding tissues and the supply line and detected in the radiometric measuring phase by the antenna. Moreover, the thermostatic liquid emits parasitic thermal noise adding to the thermal noise emitted by the heated tissues.

Moreover, this liquid screen preferably separates the measuring antenna from the surrounding tissues and hence reduces the temperature gradient between these latter and said antenna, with the result that the sensitivity of measurement of the temperature by radiometry falls.

Moreover, the thermostatic liquid circulating between the antenna and the prostate has the drawback of placing the location of the electric field, hence of the application of energy, at a maximum in the film of water and not in the prostatic tissues. The efficiency of the treatment is thereby diminished.

SUMMARY OF THE INVENTION

The present invention has for its object to overcome particularly all of the mentioned drawbacks.

To this end, it has for its object a probe for heating tissues by microwave and for the measurement of temperature by microwave radiometry, adapted to be introduced into a cavity or a conduit of the human body, permitting the destruction of the surrounding tissue, particularly prostatic tissues and tissues of the urethral wall, and comprising essentially, on the one hand, at least one elongated antenna formed by at least one conductor portion of helicoidal shape provided on a dielectric support structure and having a front end and a rear end, on the other hand, electrical connection means for the transfer of microwave signals toward and from said at least one antenna, connected to a corresponding external generator and radiometer, and, finally, a catheter covering said antenna or antennas and, as the case may be, at least the portion of electrical connection means proximal to said antenna or antennas, which probe is characterized by the fact that the dielectric support structure has or coacts with thermostatic fluid circulation means for the antenna at least present within the tubular channel delimited by said at least one helicoidal conductor portion, these means being connected to means for the supply and evacuation of said thermostatic fluid.

BRIEF DESCRIPTION OF THE DRAWINGS

The invention will be better understood from the following description which relates to preferred embodiments, given by way of non-limiting examples, and explained with reference to the accompanying schematic drawings, in which:

FIG. 1 is a side elevational view of a probe according to the invention;

FIG. 2 is a side elevational and cross-sectional view in the plane of FIG. 1 of the antenna and of the support forming a portion of the probe shown in this figure, according to a first embodiment of the invention;

FIG. 3 is a side elevational view of the support body carrying the antenna shown in FIG. 2;

FIG. 4 is a side elevational and cross-sectional view in the plane of FIG. 1 of the antenna and of the support forming a portion of the probe shown in this figure, according to a first modification of a second embodiment of the invention;

FIG. 5 is a side elevational and cross-sectional view in a plane perpendicular to the plane of FIG. 1, of the antenna and of the support forming a portion of the probe shown in this figure, according to a first modification of a second embodiment of the invention;

FIG. 6 is a view of the antenna and of the support body, identical to that of FIG. 4, according to a second modification of a second embodiment of the invention;

FIG. 7 is a view of the antenna and of the support identical to that of FIG. 5, according to a second modification of a second embodiment of the invention;

FIG. 8 is a side elevational view of the support body carrying the antenna shown in FIGS. 6 and 7;

FIGS. 9A, 9B, 9C and 9D are cross-sectional views, respectively on the lines A—A, B—B, C—C and D—D, of the central dielectric support shown in FIG. 8;

FIG. 10 is a side elevational view, on a different scale and partially in cross section, of a probe according to the invention, comprising an antenna formed according to a third embodiment of the invention;

FIG. 11 is a side elevational and cross-sectional view in the plane of FIG. 1, of the antenna and of the support body forming a portion of the probe shown in this figure;

FIG. 12 is a view on a different scale of the detail A of FIG. 11;

FIGS. 13A to 13C are perspective views showing different successive steps of a mode of production of the antenna of a probe with antenna shown in FIG. 11;

FIG. 15 is a view similar to that of FIG. 13A showing a first step in the production of antennas shown in FIG. 14.

DESCRIPTION OF THE PREFERRED EMBODIMENTS

Figure 14:
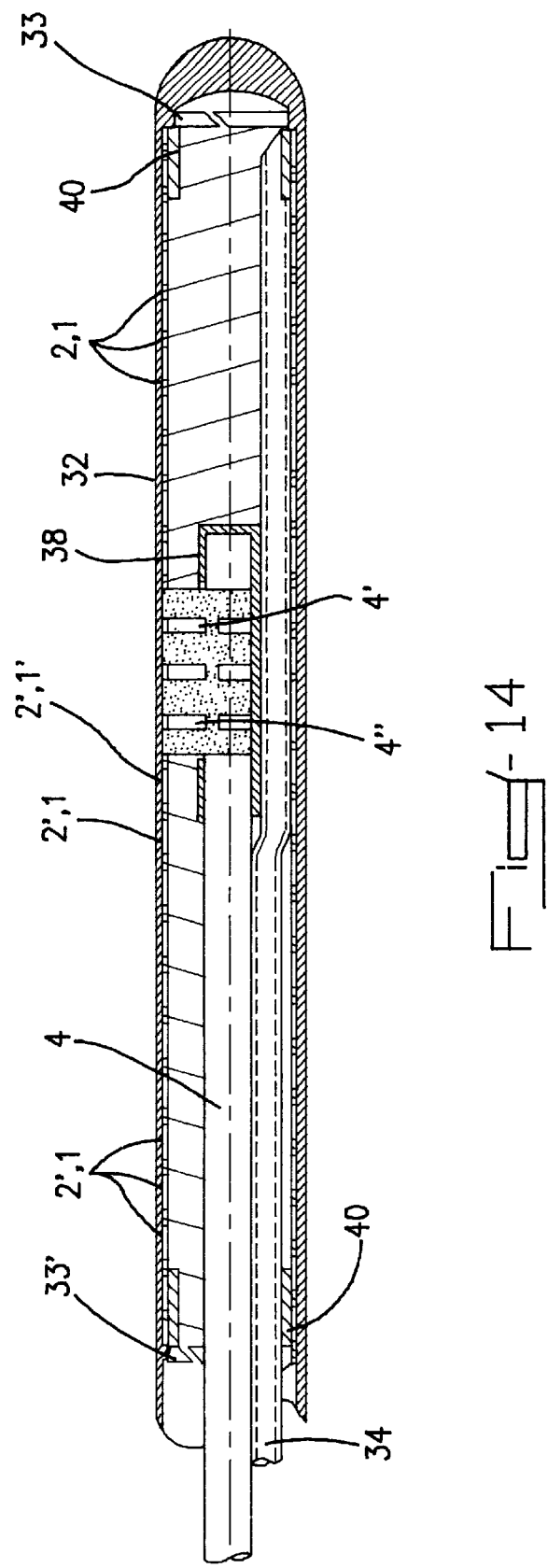
FIG. 14 is a side elevational and partially cross-sectional view of an antenna/support body assembly similar to that shown in FIG. 10, but comprising two antennae.

As is shown in FIGS. 1 and 10 of the accompanying drawings, the probe comprises essentially on the one hand at least one elongated antenna 1 formed by at least one conductive portion 2, 2' of helicoidal development provided on a dielectric support structure 3 and having one front end 3' and one rear end 3", on the other hand, electrical connection means for the transfer of microwave signals toward and from said at least one antenna 1, connected to a corresponding external generator and radiometer, and, finally, a catheter 5 covering said antenna or antennas 1 and, as the case may be, at least the portion of the electric connection means 4 adjacent said antenna or antennas 1.

In accordance with the invention, the dielectric support structure 3 has or coacts with means 7, 7', 9, 10; 19, 24; 20, 28; 32, 34 for circulation of thermostatic fluid of the antenna 1, 1' at least present within the tubular channel delimited by said at least one helicoidal conductor portion 2, 2', these means being connected to supply and evacuation means 6, 6', 6", 6"' of said thermostatic fluid.

Thanks to this arrangement, it is possible to thermally control the antenna 1 or antennas 1, 1', so as to minimize and control their own thermal noise which is detrimental to the radiometric measurement and to avoid too great a temperature elevation of the antenna 1 or antennas 1, 1' and of the supply line in the course of the emission phase, without however influencing the radiometric measurement by an absorption effect.

Moreover, it is also possible, by bringing the antenna 1 and the tissues to be treated as close together as possible, to use in an optimum manner the region of very high intensity of the high frequency electromagnetic field radiated by the antenna 1, and which is located adjacent the external envelope of this latter, for rapid necrosis of the superficial tissues, including the urethral wall, permitting suppressing the effect of pain by destruction of the microcirculation and of the nerve ends located at the surface of said tissues.

Thus, the object of the use of the probe according to the invention, by using the mentioned protocol, is to create a prostatic chamber as deep as possible.

Thus, the greater the diameter of this chamber, the better is the clinical result. Of course it is well known to a person skilled in the art, specialized in microwaves and radio frequencies, that the higher the frequency the weaker the penetration of the electromagnetic waves. This is why high ISM frequencies (for scientific and medical uses) such as for example 2450 MHz are not used according to the invention, although the cost of using this frequency is low because of its widespread public use (microwave ovens). It is therefore sought, within the scope of the invention, to use low frequencies such as particularly 434 MHz, which frequency is also authorized, which permits increasing substantially the depth of penetration and hence the depth of the prostatic compartment.

Preferably, each antenna 1, 1' is formed by two helicoidal conductor portions 2 and 2' in the form of flat metallic ribbons, connected at their adjacent ends and having opposite directions of winding from said adjacent ends, the electrical connection means 4 consisting of a coaxial cable whose connection to a microwave/radiometer generator assembly is effected via a connection cable and by means of suitable connectors.

In the case particularly of a urethral probe, and so as to ensure in precise and reproducible manner its positioning within the prostate, the catheter 5 can be provided, at the level of its front end, with means 5' expansible in the bladder for positioning the active portion of the probe in the (prostate) conduit or cavity and a means 5" for positioning and longitudinally blocking the antenna 1 or antennas 1, 1' within said catheter 5.

The means 5" could, for example, consist in a rigid or semirigid elongated element disposed in the forward portion of the catheter 5 and forming an abutment for the front end 3' of the dielectric support structure 3 so as to block this latter, during introduction of the antenna 1 into the catheter 5, in a predetermined situation relative to the expansible means 5'.

These latter could consist, for example, of a balloon inflatable by injection of a liquid or of an inflating fluid through a connector 18 (provided with a non-return valve), a flexible pipe 18' and a conduit provided in the dielectric support structure 3, or a flexible tube disposed between the antenna and the catheter and opening through an opening or a sleeve 18", at the level of the front surface of the forward end 3' of the support structure 3, in a channel 51''' provided in the elongated rigid element 5'' and communicating with the interior of said balloon 5' (see FIGS. 4 and 5).

However, the expansible means 5' could also consist in a sleeve disposed in the front end of the catheter 5 and cut off in longitudinal plates, these plates being adapted to be curved, with radial extension, to form a body in the form of a sphere, by displacement of a mandrel actuated manually, hydraulically or electrically.

The first mentioned modification leads to a probe of the Foley type and the second to a probe of the Malecot type.

To obtain a probe of small radial dimension, permitting its introduction into conduits of small cross section, all the helicoidal conductor portions 2, 2' forming the antenna 1 or antennas 1 or 1' are rolled substantially symmetrically about a same longitudinal axis (see the following drawing figures) and rest substantially on a same imaginary cylindrical surface, with a circular cross section, forming the tubular channel and within which circulates the thermostatic fluid.

So as to reduce the internal thermal noise of the coaxial cable 4 adapted to influence the radiometric measurement and to fix it at a precise known and adjustable value, it can be provided that the thermostatic fluid circulates going or preferably coming about the electrical connection means 4 in a tubular sheath 6 and by forming a longitudinal sleeve enveloping said electrical connection means 4, particularly the portion of these latter which can be situated in the cavity or conduit of the human body.

This tubular sheath 6 will preferably be connected to a connector 6' for connection to an evacuation conduit, the temperature of the evacuated thermostatic fluid being measured by suitable means for the control of the temperature of the antenna 1 or antennas 1, 1' and of the coaxial cable 4 and for a suitable correction of the radiometric measurement of temperature of the tissue.

Similarly, the supply means 6", 6''' for thermostatic fluid can consist of a sheath 6" surrounding the sheath 6 and connected to a connector 6''' for connection to a source of thermostatic fluid.

However, said supply means 6" for thermostatic fluid could also be present in the form of a flexible tube, this as a function of the shape of the fluid circulation means in the dielectric support 3 (see FIG. 2).

According to one characteristic of the invention, and so as to reduce the heat exchange between the probe and the environment tissues and to maintain a large temperature difference between said tissues and the antenna 1 or antennas 1, 1', favorable to precise radiometric measurement, said probe can preferably be covered on its external surface either with a layer or with a sheath, particularly a thermoretractable one, or the like of a thermally insulating material.

As a modification, it can also be provided that the catheter 5 itself is made of thermally insulating material.

Nevertheless, it is also desirable, for reasons given above, that the antenna 1 be located in immediate adjacency to the tissues and to do this the mentioned insulating material, for example either of the type known as polyethylene or of the type known as PTFE, is present with minimum thickness, but sufficient to constitute a thermal insulation between the antenna 1 or antennas 1, 1' and the external surface of the probe, the thickness being particularly a function of the temperature difference sought between the antenna 1 or antennas 1, 1' and the tissues adjacent to this latter.

According to a first modified embodiment of the invention, the probe has only a single antenna 1 operating for emission and reception.

However, according to a second preferred modification of the invention, the probe preferably comprises two antennae 1, 1' each formed by two helicoidal conductor portions 2, 2' and connected to the coaxial cable conductors 4 providing electrical connection means, the first antenna 1 being adapted to the frequency of emission of the microwave generator and the second antenna 1' being adapted to the reception frequency of the radiometer, each of said antennae 1, 1' having a high impedance at the adaptation frequency of the other of said antennae 1, 1'.

Thus, the actions and effects of each of the antennae 1 and 1' will be negligible at the frequency or in the range of frequencies of operation of the other of said antennae 1, 1'.

So as to reduce the size of the antennae ensemble 1, 1'/dielectric support body 3 and to have portions of conductors 2, 2' of each of said antennae 1 and 1' at minimum distance from the tissues to be treated, the windings of the helicoidal conductor portions 2, 2' forming the antenna 1' adapted to radiometric reception, are disposed between the windings of the helicoidal conductor portions 2, 2' forming the antenna 1 adapted to be emitted, the ends of the portions of the helicoidal conductor 2, 2' of the antenna 1' will thin in a progressive manner, so as to avoid points of current which could result from an abrupt cutting of the helicoidal conductor portions forming the antenna 1' of small dimension.

The thermostatic fluid circulating in the electrical support structure 3, and which preferably consists of water, can also serve for good adaptation of the antenna 1 with the Microwave generator, which emits particularly frequencies of 915 MHz or, preferably, of about 434 MHz, and with the radiometer, which is adapted to treat more particularly the thermal noise signals of frequencies comprised between 2 GHz and 4 GHz.

The same is true of course for the water in the adaptation of antenna 1' to the range of frequencies of radiometric measurement.

To this end, the quantity of thermostatic fluid, particularly water, present in the cylindrical channel formed by helicoidal conductor portions 2 and 2' is sufficient to limit the length of said conductor portions 2 and 2' to an axial length (tubular channel formed by these conductor portions) less than 8 cm, preferably less than 6 cm (particularly as concerns antenna 1), whilst permitting an optimum adaptation of the impedance of the antennas 1 and 1' to the desired operating frequencies of the microwave generator and of the radiometer (not shown).

In addition to its thermostatic role, the water present within the antenna 1 also has the effect of shortening the electrical length of this latter such that its length, particularly for an operating frequency of about 434 MHz, will not be greater than the length of the ureter situated in the prostate.

Thus, the radiating element designed to transfer the maximum energy to the prostate at 434 MHz (adaptation of impedance) will have in air a length of 17 cm which is not compatible with the length of the prostatic ureter. The presence of thermostatic fluid permits reducing the length of the antenna to about 5 cm whilst preserving an optimum impedance adaptation.

In accordance with a first embodiment of the invention, shown in FIGS. 2 and 3 of the accompanying drawings, the thermostatic fluid circulates, in the antenna 1 or antennas 1, 1', at least in part along a path parallel and adjacent to the helicoidal conductor portions 2 and 2' (with interposition of a dielectric sealed layer), following the development of these latter and being always located on the side of said portions 2 and 2' opposite the external surface of the probe.

More precisely, the dielectric support structure consists in an elongated body 3 of cylindrical shape and can have on its external surface a groove 7 of helicoidal development provided on its two lateral surfaces, adjacent the external surface of said support 3, continuous facing shoulders 8, said groove 7 being connected, on the one hand, at the level of its end near the rear end 31" of the support 3, to a supply conduit 9 for a thermostatic fluid and, on the other hand, at its end near the forward end 3' of the support 3, to a conduit 10 for evacuation of thermostatic fluid provided longitudinally within said support 3 and opening into a tubular sheath 6 surrounding the electrical connection means 4.

The groove 7, which consists of two or four portions of groove with opposed development from the medial zone of the dielectric support 3, receives the conductor portions 2 and 2' in the form of strips at the shoulders 8, on which said portions 2 and 2' can be secured by cementing their lower surface covered with a suitable insulating material.

Thus, said conductor portions 2 and 2' form together with a central throat 7' of the groove 7, located between the shoulders 8, a channel for circulation of thermostatic fluid directly adjacent said portions 2 and 2'.

According to one characteristic of the invention, the dielectric support structure 3 is preferably constituted by two support halves 11, 11' assembled coaxially by partial nesting and cementing at the medial region of the antenna 1 or antennas 1 and 1', namely, on the one hand, a first support half 11 carrying the first portion or portions of helicoidal conductor or conductors 2 and having an axial longitudinal perforation 12 for the reception of the forward portion of the coaxial cable 4 forming electrical connection means, as well as an annular support 13 for holding and blocking the front end of said coaxial cable portion 4 and, on the other hand, a second support half 11' carrying the second portion or portions of helicoidal conductor or conductors 2', said support halves 11, 11' being provided, adjacent their assembly zones, with radial passages 14, 14' in the form of slots for the passage of the ends of the helicoidal conductor portions 2, 2' for their respective connection with the central filamentary conductor 4' and the external tubular conductor 4" of the coaxial cable 4.

This axially extending perforation 12 provides an interstice in the form of a sleeve about the coaxial cable 4 for the circulation of thermostatic fluid between the conduit 10 and the sleeve 6, this latter being connected to said axial perforation 12.

As shown in FIGS. 4 to 9 of the accompanying drawings and according to a second embodiment of the invention, the elongated dielectric support 3 is constituted by an external sleeve 15 mounted on an internal mandrel 16, the external sleeve 15 carrying the helicoidal conductor portions 2 and 2' and the internal mandrel 16, having in its rear portion an elongated axial perforation 17 receiving the front portion of the coaxial cable 4 forming the electrical conduction means and connected to a tubular sheath 6 surrounding said coaxial cable 4.

The internal mandrel 16 is mounted in the external sleeve 15 with the provision of a longitudinal annular gap 19 or of longitudinal annular gap portions 20 between these two sleeves 15 and 16, the thermostatic fluid circulating in this gap 19 or these interstitial portions 20.

According to a first modification of the second embodiment of the invention, shown in FIGS. 4 and 5 of the accompanying drawings, the internal mandrel 16 is, on the one hand, provided on its external surface, and at least at the level of its longitudinal ends, with radially projecting portions 21 limited in length, disposed with regular spacing about said ends and bearing on the internal surface of the external mandrel 15 after assembly by nesting said mandrel 16 in said sleeve 15 and, on the other hand, provided with forward projecting portions 22 at the front end of said mandrel 16, bearing, after assembly, on a closure wall 23 of the front end of the external mandrel 15 and providing communication passages 22' between the annular gap 19 existing between the mandrel 16 and the sleeve 15 and a conduit 24 for evacuation of thermostatic fluid extending longitudinally within said internal mandrel 16, opening on the front surface before the mandrel 16 and connected to the axial perforation 17 receiving the front portion of the coaxial cable 4.

The thermostatic fluid is, in this modification, injected between the projecting portions 21 located at the rear end of the mandrel 16 by means of the sleeve 6".

According to a second modification of the second embodiment of the invention, shown in FIGS. 6 to 9 of the accompanying drawings, the internal mandrel 16 is provided, on its external face, with projecting portions 25 that are continuous over all the length of said mandrel 16 and delimiting between themselves annular interstitial portions 20 forming separate channels for circulation of thermostatic fluid with cross sections in portions of a ring, certain of said projecting portions 25 stopping at a distance from the wall 26 for delimitation and front closure of said channels, so as to provide, for each channel, a passage 27 between the channel in question and at least one adjacent channel, at the front end of the internal mandrel 16.

For the evacuation of the thermostatic fluid, certain of the annular interstitial portions 20 communicate, adjacent their rear ends, with the axial perforation 17 receiving the front portion of the coaxial cable 4 by means of radial openings 28, particularly in the form of oblong holes or slots.

Thus, the thermostatic fluid is injected in annular interstitial portions 20 that have no radial openings 28 and open at the rear end 3" of the support 3, and this fluid circulates toward the front end 3' to the wall 26 and is then injected through the passages 27 into the annular interstitial portions 20 provided with radial openings 28 and closed at the rear end 3" of the support 3 and circulates in these annular interstitial portions 20 to flow through said radial openings 28 into the axial perforation 17.

According to one characteristic of the invention, applicable to the two modifications described above, the internal mandrel 16 can preferably be comprised of two mandrel halves 16' and 16", assembled coaxially by a partial nesting and cementing at the medial region of the support 3, the half 16" forming the rear portion of said mandrel 16 comprising said axial portion 17 for the reception of the front portion of the coaxial cable 4 and an annular support 29 for holding and blocking the front end of the coaxial cable 4, said mandrel halves 16' and 16" being provided, adjacent their assemblage regions, with radial passages in the form of slots 14, 14' coinciding with the passages of the external sleeve 15, for the passage of the ends of the helicoidal conductor portions 2 and 2' for their connection respectively with the central filamentary conductor 4' and the external tubular conductor 4" of the coaxial cable 4.

The assembly of the two support halves 11, 11' or of the two mandrel halves 16', 16" is of course carried out in such a manner that the grooves, the passages or the conduits passing through the two halves will be continuous.

Moreover, as shown in FIGS. 2, 4, 5, 6 and 7, there can be provided, in each support half 11, 11' or mandrel half 16', 16", and at the level of the assembly regions, axial recesses forming, after assembly, a chamber 30 delimited on the one side by the support 13 or 29 and adapted to be filled, for its sealing, with a resin or like material.

This sealed chamber 30 could serve for the connection of the ends of the conductor portions 2 and 2' of the antenna 1 or antennas 1, 1' to the internal conductors 4' and external conductors 4" of the coaxial cable, thereby ensuring a reliable electrical insulation.

According to one characteristic of the invention, the helicoidal conductor portions 2 and 2', particularly of copper, can be connected by cementing in the corresponding reception grooves.

As a modification, the helicoidal conductor portions 2 and 2' can also be provided by deposition of a metallic layer, particularly of copper, followed by engraving or selective erosion forming helicoidal designs constituting said conductor portions.

According to a third embodiment of the invention, shown in FIGS. 10 to 13 of the accompanying drawings, each antenna 1, 1' is formed, together with the dielectric support structure 3, by helicoidally rolling up at least one strip portion 31 of a flexible dielectric material and comprising, within its body, a strip of conductive material 2, 2', said at least one strip portion 31 being applied against the internal wall of the forward end 31' of a tube 32 of a flexible or semirigid synthetic material, this under the action of the elastic pressure resulting from a state of residual radial compression of said at least one strip portion 31 within said tube 32.

As shown more particularly in FIG. 12 of the accompanying drawings, the strip 31 comprises a central conductive strip 2, 2' sandwiched in sealing manner between two layers of dielectric material such as, for example, polyamide (for example of the type known as CAPTON—trademark) or of polyester (for example of the type known by the designation MYLAR—trademark).

This strip 31 could preferably be cut off in a flexible printed circuit comprising several strips in parallel and used normally as connection rule.

As shown more particularly in FIG. 11 of the accompanying drawings, antenna 1 is preferably constituted by rolling up, in opposite directions, two strip portions 31, the windings of the strip portions 31 being joined to radial abutments 33, 33', for example resilient and in annular form, being disposed at the front ends 3' and rear ends 3" of the strip portions 31 forming the dielectric support structure 3 and the antenna 1.

In the case of a probe with two antennas 1 and 1', these latter are constituted by rolling up, two by two and in opposite directions, four strip portions 31, each pair of strip portions 31 comprising a longer portion and a shorter portion, the windings of the pairs of strip portions 31 being joined together and bearing against each other at the front ends 3' and rear ends 3" against the radial abutments 33, 33' (FIG. 14).

Preferably, the strip portions 31 of lesser length, adapted to form antenna 1', adapted for radiometric reception, thin progressively in the direction of their free ends.

The emplacement of the front axial abutments 33 and rear axial abutments 33' permits, on the one hand, longitudinally blocking both or the four helicoidal rolls of the strip portions 31 forming the antenna 1 and the antennas 1, 1' and, on the other hand, maintaining the longitudinal compression of said rollings in the tube 32.

The electrical connection between the conductor portions 2, 2' of the helicoidal rollings of the strips 31 and the conductors of the coaxial cable 4, forming electrical connection means, is obtained by stripping the adjacent ends of the two strip portions 31 mentioned above and connecting them to the conductors of said coaxial cable 4, the connection zone and the stripped portions of the strip portions 31 and of the coaxial cable 4 being enclosed in a sheath or sealed Insulating body 38, filled as the case may be with resin or a like insulating material.

The circulation of the thermostatic fluid is ensured, on the one hand, by the tube 32, whose front end is closed in a sealed manner and whose rear prolongation, containing the coaxial cable 4, is connected to a device 35 for injection of thermostatic fluid, and, on the other hand, by a tubular conduit 34 disposed in the tube 32 and opening at the front end of this latter, said tubular conduit 34 being connected to a device 36 for evacuation or recirculation of the thermostatic fluid.

Thermostatic fluid could for example be injected freely, by flowing through tube 32 and be drawn out, after having circulating along the coaxial cable 4 and within the tubular channel delimited by the strip portions 31, via the conduit 34 at the front end 32' of said tube 32.

This third embodiment according to the invention permits obtaining an entirely flexible and deformable probe, because of the non-rigid structure of each antenna 1, 1' and with a maximum volume of thermostatic fluid within the antenna 1 or the antennas 1 and 1'.

As shown in FIGS. 13A to 13C of the accompanying drawings, the embodiment of such a flexible probe comprising an antenna 1, can consist for example in creating electrical connections between the coaxial cable 4 and the conductor portions 2, 2' of the two strip portions 31, introducing the coaxial cable 4 into a tube 32 and the front end of said cable 4 connected to the strip portions 31 in a slotted hollow mandrel 37, whose external diameter is less than the internal diameter of the tube 32 (FIG. 13A), and rolling up in a locking manner said strip portions 31 on said mandrel 37 by blocking the two ends of the two strip portions 31 in the slot or slots of said mandrel 37, then in slipping the tube 32 on the front end of the coaxial cable 4 and on the portion of the mandrel 37 carrying the strip portions 31 until contact of said mandrel 37 with the rear abutment 33' previously mounted in the tube 32 (FIG. 13B), and then extracting the mandrel 37 from the tube 32 retaining the strip portions 31 in said tube 32 by means of a pressure sleeve 37' (at the time of retraction of mandrel 37, the strip portions 31 partially expand and apply themselves internally against the tube 32—FIG. 13C), emplacing the front abutment 33, as the case may be, by longitudinally compressing the strip portions 31 with the aid of the mandrel 37, and, finally, closing the front end 32' of the tube 32, for example by crimping the material of said tube 32 so as to form a plug 32".

The production of a probe of the type described above comprising two antennas 1 and 1' can comprise the same steps as those described above, except using two pairs of strip portions 31 of different length (FIG. 15).

So as to adjust and regulate the configuration of the radiated field, there can be, according to a complementary characteristic of the invention, provided that the probe comprises, at least at the opposite distal ends of the antenna 1 or the antennas 1, 1', supplemental members or inserts 40 of a dielectric material, for example in the form of rings, disposed in the tubular channel delimited by said at least one strip portion 31 comprising the antenna 1 or the antennas 1, 1'.

Thus it is possible, by acting on the different characteristics and the supplemental connected pieces or inserts 40, namely particularly their length, their thickness or width, the nature of the material constituting them (value of permissivity) and their emplacements, to construct probes adapted specifically to a given volume to be treated.

By preferably giving them the shape of a ring or an annulus, the free circulation of the thermostatic fluid is practically not hindered in the tubular channel formed by the antenna 1 or the antennas 1 and 1', and the flexibility of the probe (utilization of a preferably flexible dielectric material) is maintained and there is permitted an easy emplacement and certain and definitive positioning of said members or inserts 40 in said probe (external diameter determined to hold grippingly within the tubular channel), at the time of production of this latter.

Thanks to the invention, it is possible to use new techniques of thermotherapy based on operations of heating tissues that are more effective in terms of temperature rise and mean temperature of treatment.

Thus, the conventional thermotherapy technique in the field of prostate adenoma consists in heating the prostate tissues to moderate temperatures of the order of 45° C. not exceeding 50° C. in the prostate and the superficial tissues.

There is thus achieved in the prostate tissues superficial hemorrhagic suffusions and the use of these temperatures requires a treatment time of 60 minutes or more.

The antennas used are antennas of the filamentary type having a radiation lobe concentrated about its medial portion in the longitudinal direction, and limited radiation toward its ends.

In particular, the radiation is limited, and hence the heating less, at the vesicle throat at which, according to urological specialists, it is necessary on the contrary to ensure sufficient heating so as to act also at this point.

The object of the invention is hence to be able to heat in a homogeneous manner from the vesicle throat to the base of the prostate, to necrotize the superficial tissues including the urethral wall, to increase the depth of penetration so as to create a prostate chamber similar to that obtained by endoscopy resection, whilst maintaining high surface temperature.

Moreover, the treatment must be as short as possible, without requiring anesthesia.

Of course the intra-prostatic temperature control which was necessary in the prior art becomes of primary importance in this high temperature technique so as to ensure the effectiveness of treatment and safety of the patient.

The use of temperature measurement "in situ" by radiometry is hence imperative, because it avoids the use of local detectors, which is to say detectors which indicate only superficial or point temperatures in the prostate. Moreover, these local detectors must be introduced within the prostate and as a result induce trauma for the patient.

Thus, thanks to the invention, the solution used is as follows:

Use of an antenna with lines of radiating retardation of helicoidal shapes (French patent application 2 711 066) having a longitudinal radiation lobe more homogeneous relative to the filamentary antenna and permitting treating also the vesicle throat;

Decrease of the working frequency, preferably to 434 MHz, so as to increase the depth of penetration of heating (in the case of small prostates, or according to the nature of the tissues, one could if desired work at the frequency of 915 MHz);

Obtention of an intra-prostatic temperature of the order of 60° C. in the course of treatment;

Very rapid temperature rise, particularly over a time interval less than 5 minutes, so as to destroy rapidly the blood microcirculation, the nerve endings and the urethral wall;

Control of the intra-prostatic temperature by radiometric technique.

Relative to the use of an antenna with radially retarding conventional lines, obtaining the mentioned results has required the solution of the following points by the invention:

Ensuring that the superficial tissues are destroyed, hence that the antenna is located as close as possible to the urethral wall;

Ensuring that the temperature measured by radiometric means is the most reliable possible, on the one hand, by:

temperature controlling the antenna and the connection cable of the antenna by circulation of fluid so as not to take count of the thermal noise itself of the antenna or of the cable and, on the other hand, by suppressing the counting for the measurement of temperature of the thermostatic fluid in the radiometric measurement.

Reducing the length of these radiating elements by addition of a dielectric having a high $\epsilon_r$ thus, the length of a radiating element in air at 915 MHz is 8 cm and at 434 MHz the latter is 17 cm, the lengths being incompatible with the sizes of the prostate which almost never exceed 5 cm).

Limiting the thermal exchanges by thermal conduction between the prostate and the thermostatic fluid.

In practice, the choice of the dielectric will be water which has relatively high dielectric losses (high heating, hence water circulation required) but also a high constant dielectric value (of the order of 80) at the frequencies used.

The complicated problem solved by the invention therefore consists in the use of a circulation of thermostatic fluid from the antenna and the connection cable so as to make reliable the radiometric measurement and to decrease the length of the antenna in the case of the use of a frequency of 434 MHz, whilst placing the antenna as close as possible to the urethral wall so as to avoid measurement of temperature of the thermostatic fluid by the radiometer and to deliver the maximum energy into the prostate to obtain a superficial and deep necrosis of the prostatic tissues.

Of course, the invention is not limited to the embodiments described and shown in the accompanying drawings. Modifications remains possible, particularly as to the construction of the various elements or by substitution of technical equivalents, without thereby departing from the scope of protection of the invention.

What is claimed is:

1. In a probe for microwave heating of tissue and for temperature measurement by microwave radiometry, said probe adapted to be introduced into a cavity or a conduit of a human body, permitting destruction of surrounding tissue, prostate tissue, and urethral wall, and comprising:

at least one elongated antenna formed by at least one conductor portion rolled up in a helicoidal configuration on an elongated dielectric support structure having a front end and a rear end;

electrical connection means for transferring microwave signals toward and from said at least one antenna connected to a corresponding external generator and radiometer; and a catheter covering said antenna and at least one portion of the electrical connection means adjacent said antenna;

the improvement wherein the dielectric support structure includes means for circulating thermostatic fluid of the antenna at least present within a tubular channel delimited by said at least one helicoidal conductor portion, said means for circulating thermostatic fluid being operatively connected to means for supplying and evacuating said thermostatic fluid.

2. The probe according to claim 1, wherein each antenna is comprised of two helicoidal conductor portions in the form of flat metallic ribbons, connected at their adjacent ends and being rolled up in opposite directions from said adjacent ends, the electrical connection means consisting of a coaxial cable.

3. The probe according to claim 1, wherein the antenna is covered at its external surface with a layer of a thermally insulating material.

4. The probe according to claim 1, wherein the catheter is of a thermally insulating material.

5. The probe according to claim 4, wherein the thermally insulating material has a minimum thickness sufficient to constitute a thermal insulation between the antenna and an end surface of the probe.

6. The probe according to claim 1, further comprising means for positioning and longitudinally blocking the antenna in said catheter, and wherein the catheter includes, at its front end, expansible means for positioning the probe in the cavity or the conduit.

7. The probe according to claim 1, wherein the thermostatic fluid circulates to and fro about the electrical connection means in a tubular sheath by forming a longitudinal sleeve enveloping said electrical connection means including the portion of said electrical connection means adapted to be located in the cavity or the conduit of the human body.

8. The probe according to claim 1, wherein the generator emits microwaves at frequencies of about 915 MHz or 434 MHz, and the radiometer is adapted to process frequencies comprised between 2 GHz and 4 GHz.

9. The probe according to claim 1, wherein the electrical connection means comprise a coaxial cable having a central filamentary conductor and an external tubular conductor, said probe comprising two antennae each formed by two helicoidal conductor portions and connected to the conductors of the coaxial cable, the first antenna being adapted to the emission frequency of the microwave generator, and the second antenna being adapted to the radiometric reception frequency, each of said antennae having a high impedance at the adaptation frequency of the other of said antennae.

10. The probe according to claim 9, wherein the windings of the helicoidal conductor portions forming the second antenna are disposed between the windings of the helicoidal conductor portions forming the first antenna, the ends of the helicoidal conductor portions of the second antenna thinning progressively.

11. The probe according to claim 9, wherein the tubular channel delimited by the helicoidal conductor portions is structured and arranged to hold a quantity of thermostatic fluid sufficient to limit the length of the conductor portions to an axial length less than 8 cm whilst permitting optimum impedance adaptation of the antennae to the desired operating frequencies of the microwave generator and of the radiometer.

12. The probe according to claim 1, wherein the thermostatic fluid circulates at the antenna, at least in part, along a path parallel and adjacent to the helicoidal conductor portions, whilst being always located on the side of said conductor portions opposite the external surface of the probe.

13. The probe according to claim 12, wherein the dielectric support structure consists of an elongated cylindrical support having on its external surface a groove of helicoidal development, said groove having on its two lateral surfaces, adjacent the external surface of said support, continuous facing shoulders, said groove being connected at its end near the rear end of the support to a supply conduit for thermostatic fluid and at its end near the front end of the support to an outlet conduit for the evacuation of thermostatic fluid, disposed longitudinally in said support, and opening into a tubular sheath surrounding the electrical connection means.

14. The probe according to claim 13, wherein the electrical connection means comprise a coaxial cable having a central filamentary conductor and an external tubular conductor, and the dielectric support structure is constituted by a first support half and a second support half, said support halves being assembled coaxially by partial nesting and cementing at a medial region of the antenna, the first support half carrying a first portion of the helicoidal conductor and having a longitudinal axis perforation for receiving a front portion of the coaxial cable and an annular support for holding and blocking a forward end of the coaxial cable, and the second support half carrying a second portion of the helicoidal conductor, said support halves having adjacent their assembly, zones with slotted radial passages for the passage of the ends of the helicoidal conductor portions for connecting these ends respectively with the central filamentary conductor and the external tubular conductor of the coaxial cable.

15. The probe according to claim 1, wherein the electrical connection means comprise a coaxial cable having a central filamentary conductor and an external tubular conductor, and the elongated dielectric support is constituted by an external sleeve mounted on an interior mandrel, the external sleeve carrying the helicoidal conductor portions and the internal mandrel having in its rear portion an elongated axial perforation receiving a front portion of the coaxial cable and connected to a tubular sheath surrounding said coaxial cable.

16. The probe according to claim 15, wherein the internal mandrel is mounted in the external sleeve thereby defining a longitudinal annular gap between the internal mandrel and the external sleeve for circulating the thermostatic fluid in said gap.

17. The probe according to claim 16, wherein the internal mandrel has on its external surface and at least at its longitudinal ends, radially projecting portions limited in length, disposed with a regular spacing about said longitudinal ends, and bearing on the internal surface of the external sleeve after assembly by nesting of said mandrel in said sleeve, and frontal projecting portions at a front end of said mandrel, bearing after assembly, on a closure wall of a front end of the external sleeve and providing communication passages between the annular gap and an outlet conduit for evacuation of thermostatic fluid extending longitudinally within said internal mandrel, opening on the front surface of the mandrel and connected to the axial perforation.

18. The probe according to claim 15, wherein the internal mandrel is mounted in the external sleeve thereby defining longitudinal annular interstitial portions between the internal mandrel and the external sleeve for circulating the thermostatic fluid in said interstitial portions.

19. The probe according to claim 18, wherein the internal mandrel has, on its external surface, projecting portions continuous over all the length of said mandrel, and delimiting between said projecting portions the annular interstitial portions forming separated channels for circulation of thermostatic fluid with part annular cross section, a number of said projecting portions stopping at a distance from a wall delimiting and frontally closing said channels, so as to provide, for each channel, a passage between the channel in question and at least one adjacent channel, at the front end of the internal sleeve.

20. The probe according to claim 19, wherein a number of the annular interstitial portions communicate adjacent their rear ends with the axial perforation via radial openings in the form of oblong holes or slots.

21. The probe according to claim 15, wherein the internal mandrel comprises a first mandrel half and a second mandrel half, said mandrel halves being assembled coaxially by partial nesting and cemented at a medial region of the support, the first half forming a rear portion of said mandrel comprising said axial perforation and an annular support for holding and blocking a front end of the coaxial cable, said mandrel halves having adjacent their assembly regions, radial slotted passages coinciding with passages of the external sleeve for the passage of the ends of the helicoidal conductor portions for connecting these ends respectively with the central filamentary conductor and the external tubular conductor of the coaxial cable.

22. The probe according to claim 1, wherein the helicoidal conductor portions are of copper and are cemented by cementing the corresponding reception grooves.

23. The probe according to claim 1, wherein the helicoidal conductor portions are formed by deposit of a metallic layer of copper followed by engraving or selective erosion.

24. The probe according to claim 1, wherein each antenna is formed, together with the dielectric support structure, by helically rolling up at least one strip portion of a flexible dielectric material and comprising in its body a strip of conductive material, said at least one strip portion being applied against the internal wall of a front end of a tube of a flexible or semirigid synthetic material, under the action of elastic pressure resulting from a residual radial compression state of said at least one strip portion in said tube.

25. The probe according to claim 24, wherein the antenna is constituted by rolling up in opposite directions, two strip portions, the windings of the strip portions being joined to radial abutments disposed at a front end and rear end of the strip portions forming the dielectric support structure and the antenna.

26. The probe according to claim 24, comprising two antennae, and wherein the antennae are constituted by rolling up, two by two and in opposite directions, four strip portions, each pair of strip portions comprising a longer and a shorter portion, the windings of the pair of strip portions being joined and bearing at their front ends and rear ends against radial abutments.

27. The probe according to claim 26, wherein the strip portions of lesser length, intended to form an antenna adapted for radiometric reception, thin progressively in the direction of their free ends.

28. The probe according to claim 24, wherein the circulation of the thermostatic fluid is ensured by the tube, whose front end is closed in a sealed manner and whose rear prolongation, containing the coaxial cable, is connected to a first device for injection of thermostatic fluid, and by a tubular conduit disposed in the tube and opening at the front end of said tube, said tubular conduit being connected to a second device for the evacuation or recirculation of the thermostatic fluid.

29. The probe according to claim 24, further comprising, at opposite distil ends of the antenna, supplemental members of a dielectric material in the form of rings, disposed in the tubular channel delimited by said at least one strip portion providing the antenna.

* * * * *